US00PP12666P2

(12) United States Plant Patent
Briant

(10) Patent No.: US PP12,666 P2
(45) Date of Patent: Jun. 4, 2002

(54) WEIGELA PLANT NAMED 'BRIGELA'

(75) Inventor: Andre Briant, Saint-Barthelemy D'Anjou (FR)

(73) Assignee: Selection New Plant Sarl, Le Luc (FR)

( * ) Notice: Subject to any disclaimer, the term of this patent is extended or adjusted under 35 U.S.C. 154(b) by 0 days.

(21) Appl. No.: 09/318,120

(22) Filed: May 25, 1999

(30) Foreign Application Priority Data

Feb. 5, 1999 (FR) ..... 016531

(51) Int. Cl.[7] ..... A01H 5/00
(52) U.S. Cl. ..... Plt./226
(58) Field of Search ..... Plt./226

(56) References Cited

U.S. PATENT DOCUMENTS

PP492 P * 11/1941 Cumming ..... Plt./226

* cited by examiner

*Primary Examiner*—Bruce R. Campell

*Assistant Examiner*—W C Baker

(74) *Attorney, Agent, or Firm*—Burns, Doane, Swecker & Mathis, L.L.P.

(57) ABSTRACT

A new and distinct red-flowered *Weigela hybrida* cultivar is provided that originated as a spontaneous mutation of unknown causation of the 'Bristol Ruby' cultivar (U.S. Plant Pat. No. 492). The new cultivar can be readily distinguished by the presence of attractive variegated foliage which is yellow-green towards the center with a lighter yellow-green and/or yellow margin and a reddish edge, and a compact growth habit. The plant vigor is good and the new cultivar is well suited for growing in U.S.D.A. Hardiness Zones 5 to 8.

3 Drawing Sheets

SUMMARY OF THE INVENTION

The previously available Weigela cultivars are recognized to constitute a group of opposite-leaved deciduous flowering shrubs that are grown to provide ornamentation in the landscape.

The new *Weigela hybrida* cultivar of the present invention was discovered during 1989 as a spontaneous mutation of unknown causation among two year-old plants of the 'Bristol Ruby' cultivar (U.S. Plant Pat. No. 492) being grown at Andre Briant Jeunes Plants at Saint-Barthelemy D'Anjou, France. More specifically, such mutation was discovered as a single distinctive branch that appeared on a single plant of the 'Bristol Ruby' cultivar.

I was attracted to the new cultivar primarily because of the attractive distinctive variegated appearance of the foliage that has proven to be stable and reliably present. Had I not discovered and preserved the new cultivar of the present invention it would have been lost to mankind.

It was found that the new *Weigela hybrida* cultivar of the present invention posseses the following combination of characteristics:

(a) Forms attractive red flowers that tend to fade as they mature, (b) Forms attractive variegated foliage that is yellow-green towards the center with a lighter yellow-green and/or yellow margin and a reddish edge unlike its 'Bristol Ruby' parent cultivar (U.S. Plant Pat. No. 492), (c) Exhibits a more compact growth habit than the 'Bristol Ruby' cultivar, and (d) Exhibits good vigor.

The distinctive variegated foliage and compact growth habit can be used to well distinguish the new cultivar from its parent.

The new cultivar well meets the needs of the horticultural industry. It is particularly well suited for providing unique ornamental planting.

The new cultivar has been asexually reproduced through the use of softwood cuttings at Saint-Barthelemy D'Anjou, France, beginning in 1990. Such propagation has shown that the characteristics of the new cultivar are strictly transmissible from one generation to another.

The new cultivar of the present invention has been named the 'Brigela' cultivar and is being marketed under the FRENCH LACE trademark.

BRIEF DESCRIPTION OF THE PHOTOGRAPH

The accompanying FIG. 1 shows during the summer a three year-old plant of the new cultivar while being grown outdoors at Saint-Barthelemy D'Anjou, France. The attractive variegated foliage together with the five-lobed red blossoms that commonly are disposed in pairs are displayed.

DETAILED DESCRIPTION

The description is based on the observation plants of the new cultivar growing outdoors at Saint-Barthelemy D'Anjou, France. Such plants had been asexually reproduced through the use of softwood cuttings. The color terminology utilized in description that follows is to be accorded its ordinary dictionary significance.

Figure 1:
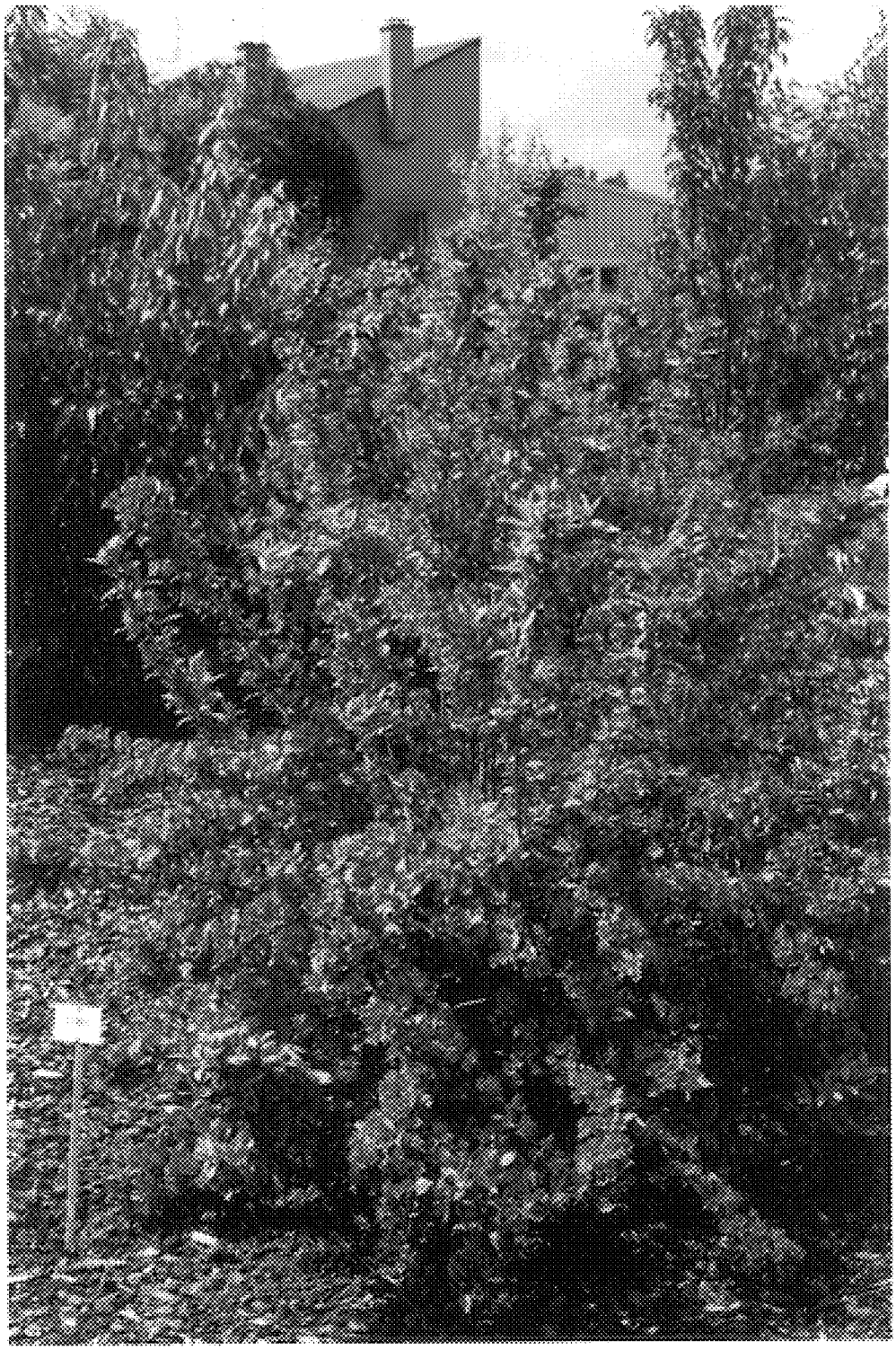
Figure 2:
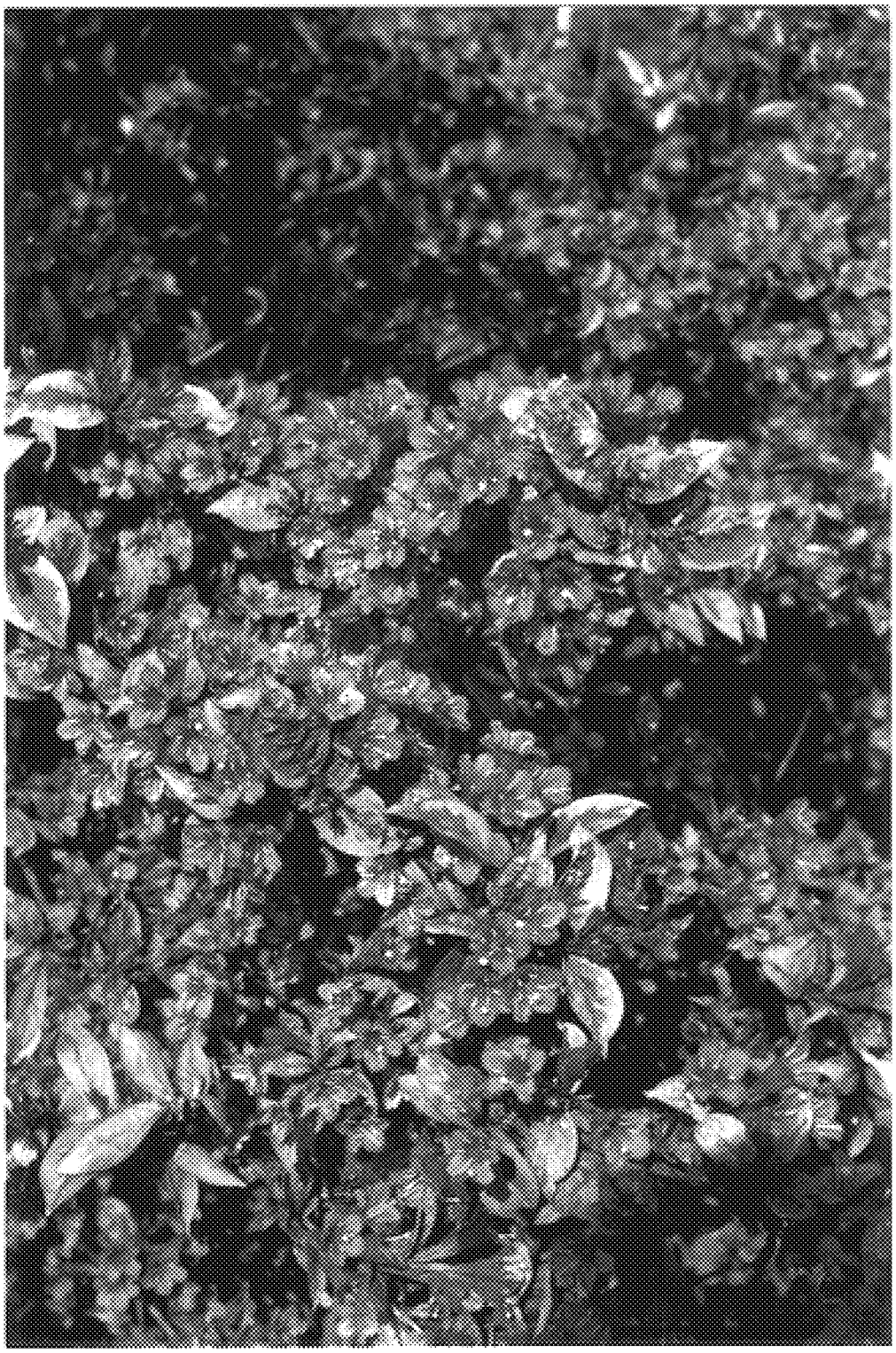
FIG. 2 depicts the variegated foliage together with the five-lobed red blossoms that commonly are disposed in pairs.
Figure 3:
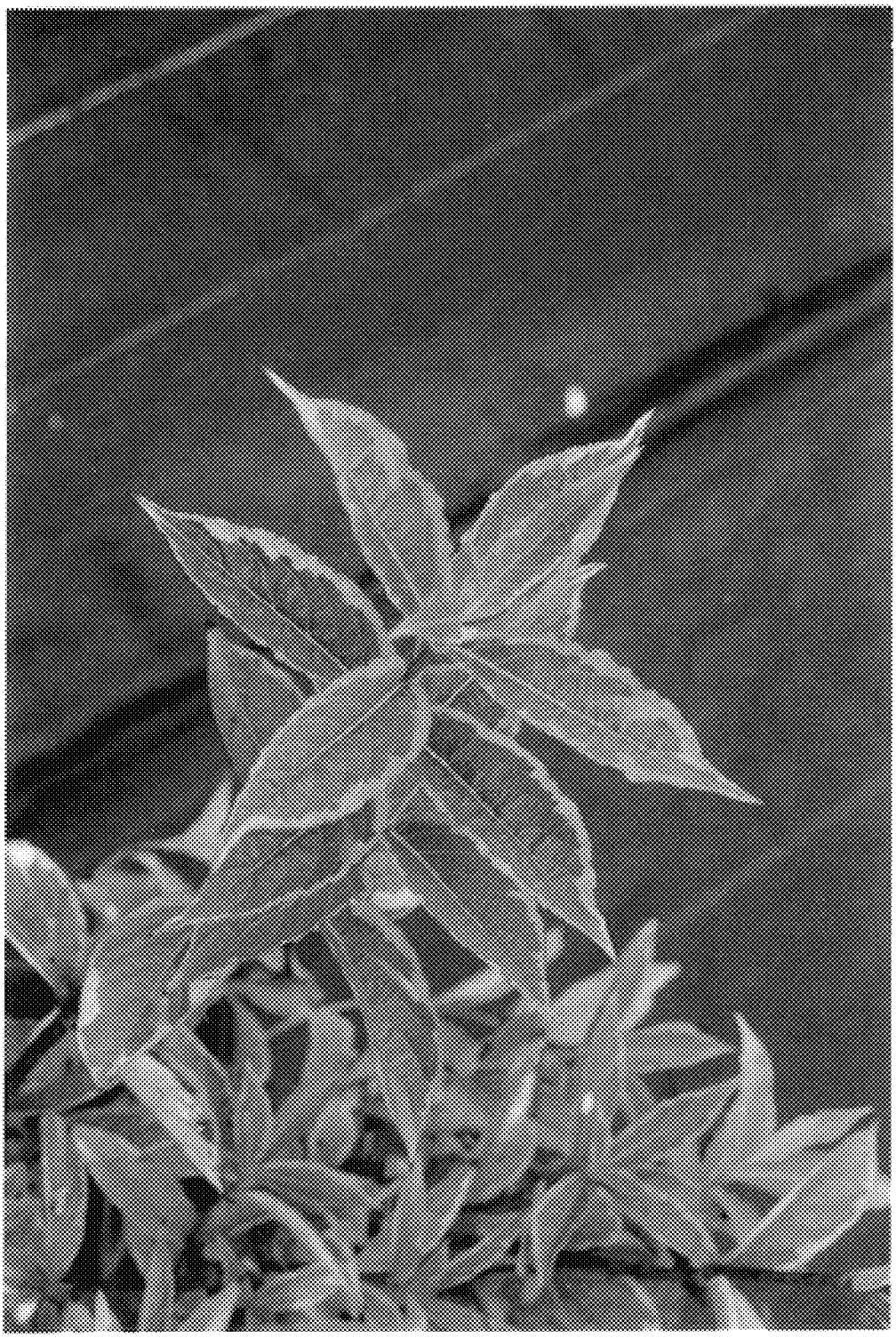
FIG. 3 depicts a closer view of the attractive variegated foliage that is light green towards the center with a yellow-green margin and a reddish edge.

Origin: Spontaneous branch mutation.
Parentage: 'Bristol Ruby' cultivar (U.S. Plant Pat. No. 492).
Classification: *Weigela hybrida*, cv. 'Brigela'.
Plant:
*Form.*—Flowering shrub.
*Height.*—Approximately 1.5 to 1.75 meters at the age of 5 years, and estimated to be approximately 1.75 to 2.5 meters when fully mature.
*Width.*—Approximately 1.5 to 1.75 meters at the age of 5 years, and estimated to be approximately 1.75 to 2.5 meters when fully mature.
Foliage:
*Disposition.*—Opposite.
*Configuration.*—Generally elliptic.
*Base.*—Cuneate to attenuate.
*Tips.*—Somewhat cuspidate.
*Margins.*—Finely toothed as illustrated in FIG. 3.
*Color.*—Variegated (as illustrated) with yellow-green coloration towards the center with light yellow-green and/or yellow margins and a reddish edge (Red Group 45A). This can be readily distinguished from the foliage of the parent 'Bristol Ruby' cultivar which is lacking in variegation.
*Leaf size.*—Approximately 9 cm. in length and approximately 5 cm. in width.
*Pubescence.*—Present on leaf surfaces.
*Petioles.*—Short.
Inflorescence:
*Buds.*—Oblong and approximately 17 mm in length and approximately 6 mm in width. The coloration is Red-Purple Group 60A.
*Disposition.*—Commonly born in pairs.
*Configuration.*—Five-lobed.
*Size.*—Approximately 3 to 4 cm. in length and approximately 3 cm. in width.
*Quantity.*—Approximately 30 flowers on a branch having a length of 30 cm.
*Color.*—Red-Purple Group 60B with some fading as the blossoms mature.
*Stamens.*—Red-Purple Group 57D in coloration.
*Anthers.*—Orange-White Group 159B in coloration.
*Fragrance.*—None.
*Blooming habit.*—Substantially the same as the parent 'Bristol Ruby' cultivar. Approximately May $10^{th}$ to June $10^{th}$.
*Sepals.*—Five in number and commonly united at the base. The length is approximately 12 mm and the width is approximately 3 mm. A combination of green and red in coloration.
*Pedicels.*—Approximately 17 mm in length, and a combination of green and red in coloration.
*Pollen.*—None formed.
Hardiness: Grows well in U.S.D.A. Hardiness Zone Nos. 5 to 8.
Disease resistance: No particular disease susceptibility has been noted during observations to date.

I claim:

1. A new and distinct *Weigela hybrida* cultivar having the following combination of characteristics:

(a) Forms attractive red flowers that tend to fade as they mature, (b) Forms attractive variegated foliage that is yellow-green towards the center with a lighter yellow-green and/or yellow margin and a reddish edge unlike its 'Bristol Ruby' parent cultivar (U.S. Plant Pat. No. 492), (c) Exhibits a more compact growth habit than the 'Bristol Ruby' cultivar, and (d) Exhibits good vigor;

substantially as illustrated and described.

* * * * *